United States Patent [19]
Ryder

[11] 3,939,968
[45] Feb. 24, 1976

[54] CONTACT LENS CAPSULE WITH INDICATING MEANS

[75] Inventor: Francis E. Ryder, Barrington, Ill.

[73] Assignee: Ryder International Corporation, Barrington, Ill.

[22] Filed: Sept. 30, 1974

[21] Appl. No.: 510,639

[52] U.S. Cl. ............... 206/5.1; 73/358; 116/114.5; 206/306; 206/459
[51] Int. Cl.² .................. A45C 11/00; G01K 11/00; G01D 21/00; B65D 85/38
[58] Field of Search ............ 206/5.1, .83, 459, 306, 206/212; 190/16; 73/358; 116/114.5

[56] References Cited
UNITED STATES PATENTS

| | | | |
|---|---|---|---|
| 929,074 | 7/1909 | Brown et al. | 190/16 |
| 2,046,863 | 7/1936 | Allphin | 73/358 |
| 3,054,378 | 9/1962 | Bienfait | 116/114.5 |
| 3,175,401 | 3/1965 | Geldmacher | 73/358 |
| 3,192,771 | 7/1965 | Stearns | 73/358 |
| 3,518,961 | 7/1970 | Kovac | 73/358 |
| 3,770,113 | 11/1973 | Thomas | 206/5.1 |
| 3,844,410 | 10/1974 | Cook | 206/.83 |

Primary Examiner—William T. Dixson, Jr.
Attorney, Agent, or Firm—Olson, Trexler, Wolters, Bushnell & Fosse, Ltd.

[57] ABSTRACT

A contact lens holder is provided with a pair of receptacles to receive a pair of contact lenses for holding them in place while they are inserted into a container. The container has liquid therein to be heated to a sterilization temperature, thereby sterilizing the contact lenses. A relatively movable vessel is positioned within the container and held in a desired position during the heating operation. The vessel is formed of transparent material and contains a quantity of eutectic material viz. a material having a specified melting point. At the outset of the sterilization process the vessel is positioned such that the eutectic material, solid at temperatures below the sterilizing temperature, is at top of the vessel. The eutectic material melts once the sterilization temperature is reached and will flow to the bottom of the vessel, thereby indicating that the sterilization temperature has in fact been reached upon subsequent cooling and removal of the holder. Since the eutectic material solidifies upon cooling, subsequent reuse of the contact lens holder requires only that the vessel be inverted to again place the solid eutectic material at the top of the vessel.

4 Claims, 5 Drawing Figures

CONTACT LENS CAPSULE WITH INDICATING MEANS

BACKGROUND OF THE INVENTION

This invention relates generally to holders for receiving contact lenses, and more particularly to indicating means to be employed with holders to provide the user with an indication that the sterilizing temperature has been reached.

Contact lenses, both of the hard and soft type, often must be sterilized before they are suitable for use. The large numbers of different lens prescription often encountered by doctors and manufacturers require that the individual pairs of contact lenses be maintained separate. To this end, each pair of contact lenses is inserted into a separate container which may also have receptacles therein for holding the right and left lens spaced apart so they do not become confused. These containers are commonly referred to as contact lens holders. A quantity of fluid is then administered to the container and then the container is placed in an autoclave or boiler for heating the fluid to a sterilization temperature. The fluid within the container is in direct contact with the lenses and effects sterilization thereof. After the sterilization temperature has been reached, the contact lens holders are removed from the heating apparatus and allowed to cool sufficiently to enable removal of the contact lenses. One common type of contact lens holder which is used for the sterilization of contact lenses is shown in U.S. Pat. No. 3,770,113. One problem presently encountered with this and other types of holders is that it is virtually impossible to determine whether or not the lens have been heated sufficiently to reach the sterilization temperature. Should the heating apparatus malfunction, or the heating cycle be of insufficient duration to raise the temperature of the fluid within the holder to the desired sterilization temperature, there will be no sterilization of the contact lenses. This condition can go undetected and therefore may cause irritation or infection to the user of the unsterilized contact lenses.

The present invention, as will be explained more fully hereinafter, is concerned with overcoming the problem inherent in the prior art. More specifically, the present invention provides means which will indicate to a user whether or not the proper sterilization temperature was in fact reached.

SUMMARY OF THE INVENTION

Accordingly, it is an object of this invention to provide a new and improved contact lens holder which can be subjected to high temperatures to cause sterilization of contact lenses placed therein and which overcomes the problems presently encountered with present contact lens holders.

Another object of this invention is to provide a new and improved contact lens holder which will provide an indication that the sterilization temperature has been reached during the heating operation.

Still another object of this invention is to provide a contact lens holder with indicating means to indicate that a sterilization temperature has been reached and which indicating means can be reset for reuse during a subsequent sterilization period.

A further object of this invention is to provide a new and improved contact lens holder which is simple and inexpensive to manufacture but has a high degree of reliability and efficiency when used.

Briefly, a contact lens holder embodying the present invention may include a container having a pair of receptacles for receiving a pair of contact lenses. The receptacles may be marked or fashioned to enable the user to identify the right lens from the left lens when inserted and removed. Associated with the contact lens holder is a transparent vessel containing a quantity of eutectic material, such as a wax with a specific melting point. The vessel is partially filled with this eutectic material. The eutectic material is of a character to be substantially solid at all temperatures below the sterilization temperature of the contact lenses and then liquify at the sterilization temperature. The vessel is initially positioned within the lens holder so that the solid eutectic material is at the upper portion of the vessel. The melting of the eutectic material causes it to flow to the bottom portion of the vessel, which indicates that the sterilization temperature has been reached. When the container is removed from the heating apparatus and opened, after cooling, the user can visually inspect the vessel to see that the eutectic material has melted and fallen to the bottom half of the vessel. The indicating vessel can be used again by rotating the vessel 180° so that the now solid mass of eutectic material is again at the top of the vessel.

Many other objects, features and advantages of this invention will be more fully realized and understood from the following detailed description when taken in conjunction with the accompanying drawings wherein like reference numerals throughout the various views of the drawings are intended to designate similar elements and components.

DETAILED DESCRIPTION OF THE ILLUSTRATED EMBODIMENT

Figure 1:
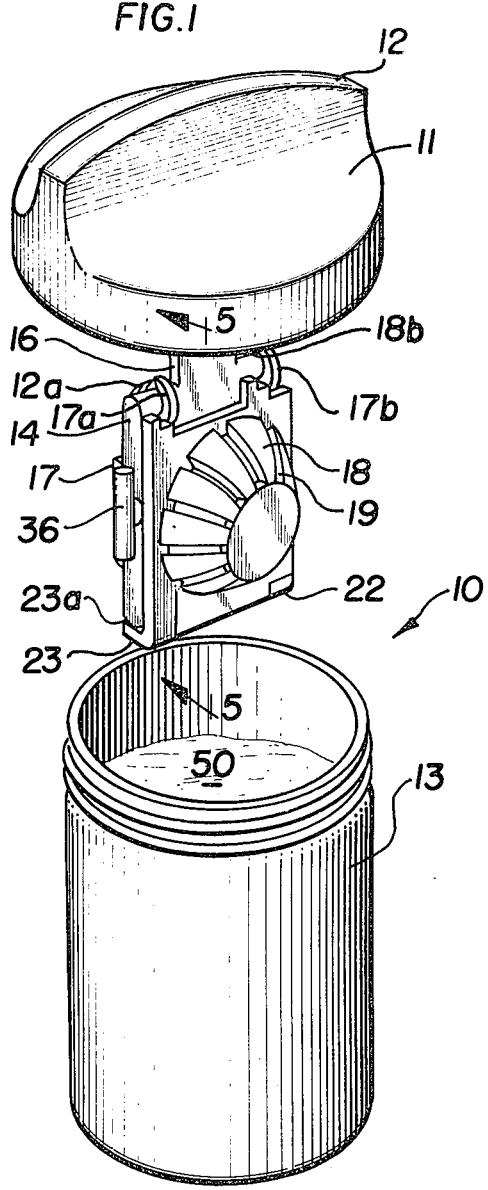
FIG. 1 is a perspective view of a contact lens holder constructed in accordance with the principles of this invention and showing the lens receptacles secured to the cap and removed from the container of the lens holder.

Referring now to FIG. 1 there is seen an exploded view of a contact lens holder constructed in accordance with the principles of this invention and designated generally by reference numeral 10. The contact lens holder 10 includes a cap 11 having a raised finger-gripping portion 12 to facilitate the user to threadedly fasten and unfasten the cap to a container body 13. The cap 11 and container body 13 are there illustrated as being substantially cylindrical in configuration. It will be understood, however, that other configurations can be utilized, such as a rectangular or square body having a snap-open cap. Secured to the cap 11 is a central support member 14. The support member 14 has a stem portion 16 extending upwardly therefrom to be inserted into a correspondingly shaped slot, not shown, formed in the underside portion of the cap 11. The central support 14 may be removed from the cap if desired.

Figure 2:
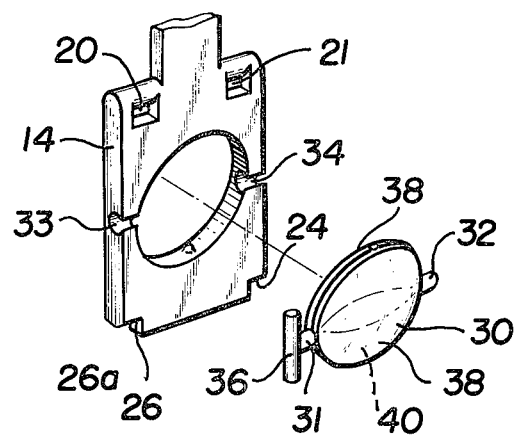
FIG. 2 is a fragmentary perspective view of a central support of the lens holder and illustrates the transparent vessel for containing the eutectic material material therein.
Figure 3:
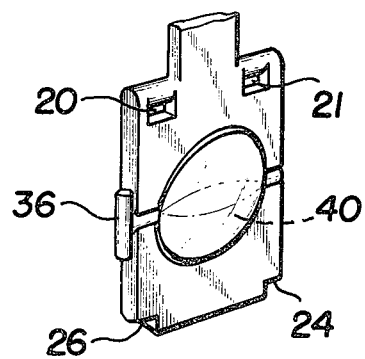
FIG. 3 illustrates the central support and vessel in an assembled condition.
Figure 4:
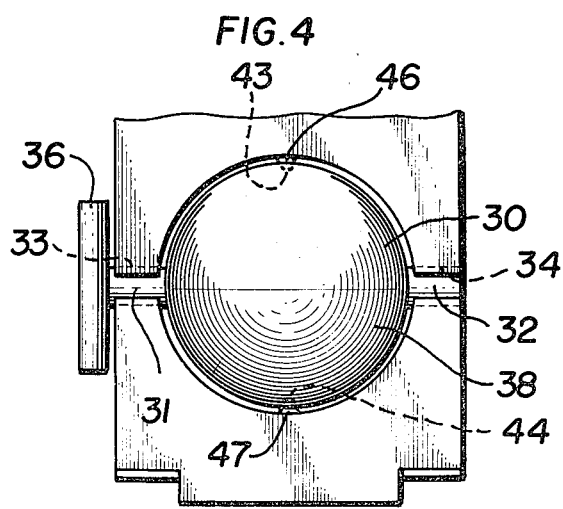
FIG. 4 is an enlarged fragmentary view showing the vessel secured to the central support and held in place by protuberances extending into detents formed in the vessel.

A pair of cup-shaped cover members 17 and 18 are hingedly secured to the central support 14. The covers 17 and 18 cooperate with the central support to form a pair of spaced apart receptacles. The cover members 17 and 18 have C-shaped hook portions 17a, 17b and 18a, 18b, respectively, formed at their upper ends to be inserted into openings 20 and 21 formed within the central support 14, as best seen in FIGS. 2 and 3. In a well-known manner the C-shaped hook members 17a, 17b and 18a, 18b are sufficiently long so that they remain at all times engaged in the openings 20 and 21 as the cover members 17 and 18 are raised upwardly. The extent of pivotal movement of the covers is limited by the fact that they abut the peripheral margin of the cover 11 before the hooks 17a, 17b or 18a, 18b can not become dislodged from the openings 20 and 21. However, by removing the central support 14 from the cap 11 the covers 17 and 18 can be pivoted a sufficient distance to enable the hooks 17a, 17b and 18a, 18b to be disconnected from the openings 20 and 21, thereby allowing the covers to be removed from the central support if desired.

Contact lenses are placed beneath the covers 17 and 18 and supported between the respective covers and the central support 14. In the illustrated embodiment the covers 17 and 18 are provided with slots 19a and 19b, respectively, to enable fluid within the container 13 to come in contact with the lenses. To insure that the covers do not open, and the contact lenses fall out, a latch portion 22 is formed on the cover 17 and a latch portion 23 is formed on the cover 18. The latch portions 22 and 23 engage recesses 24 and 26, respectively, formed on the central support 14, as best seen in FIGS. 2 and 3. The latch means 22 and 23 may be provided with raised portions, as indicated by reference numeral 23a to snap over a tapered endwall portion of the notches, as indicated by reference numeral 26a. The central support 14 forms a common wall between the receptacles formed by the covers 17 and 18.

To this point the basic design of the lens holder 10 is similar to that as shown in U.S. Pat. No. 3,770,113. The present invention improves over the design as described in said patent in the provision of means to indicate that the sterilization temperature has been reached. Generally, this function is provided by a vessel 30 which serves a dual purpose in that said vessel contains the eutectic material mentioned previously, and also provides convex supporting surfaces for the lens elements, best illustrated in FIG. 5.

In accordance with the disclosed embodiment of the invention a vessel 30 has a pair of diametrically opposed pin elements 31 and 32, and the central support has a pair of diametrically opposed sockets 33 and 34. The pin elements 31 and 32 are inserted into the sockets 33 and 34, respectively, so that the vessel can rotate about the axis of the pin elements. To facilitate rotation of the vessel 30 the pin element 31 is provided with a T-handle portion 36. Preferably, the vessel 30 is formed of high temperature molded clear plastic elements or halves 37 and 38 which are secured together along a seam formed at their interface 39. A pair of detents 43 and 44 are formed on opposite sides of the vessel 30 and arranged to be substantially perpendicular to the axis of the pins 31 and 32. The detents engage protuberances 46 and 47, respectively, to hold firmly the vessel in a vertical position relative to the central support 14 and to insure that the vessel will not inadvertently rotate during use.

Most advantageously, a quantity of eutectic material 40 is contained within the vessel 30, and the eutectic material preferably has a melting temperature equal to the sterilization temperature to be obtained within the container 13.

Figure 5:
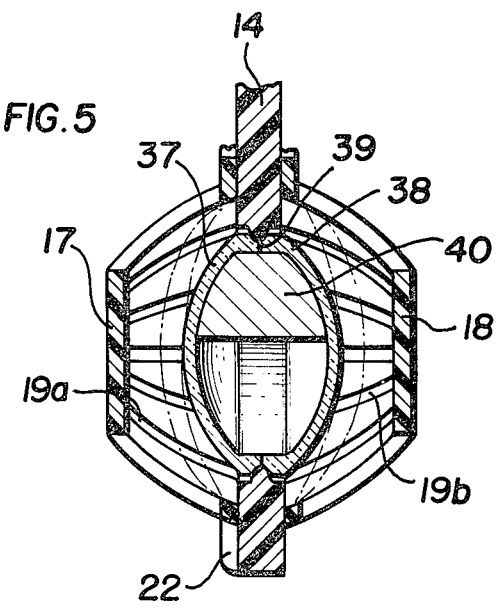
FIG. 5 is a fragmentary sectional view taken along line 5–5 of FIG. 4.

Pursuant to a standard type of sterilization procedure, a quantity of liquid 50 is placed within the container 13, this liquid either being a disinfectant or plain water. Contact lenses, indicated in phantom line in FIG. 5, are placed beneath the covers 17 and 18 and captured within the receptacle formed thereby, resting on the convex surfaces of vessel 30. The covers are locked in place by the latch portions 22 and 23. The central support 14 together with the vessel 30 and contact lenses held by the covers 17 and 18, are inserted into the container 13 and the cap 11 is tightened. The contact lens holder 10 is then placed in a heating unit, such as an autoclave or boiler so that the temperature of the liquid within the container is raised to a sterilization temperature. The position of the vessel 30 is such that at the initial portion of the sterilization cycle the eutectic material 40 is placed at the top of the vessel. When the temperature of the liquid within the container reaches the sterilization temperature desired, the eutectic material 40 will melt and flow to the bottom of the vessel. After the lens holder 10 has cooled and been opened for removal of the contact lenses a simple visual inspection of the vessel will enable the user to determine readily whether or not the sterilization temperature has been reached, this being indicated by the presence of the eutectic material at the bottom of the vessel.

When it is again desired to use the lens holder to sterilize lenses, the vessel 30 is rotated about the axis of the pins 31 and 32 to again place the eutectic material at the top of the vessel. A subsequent sterilization is then performed and the eutectic material will again melt and flow to the bottom of the vessel. Should a malfunction of the heating apparatus occur the eutectic material will not melt. Therefore the eutectic material will remain in the upper portion of the vessel. This then will indicate to the user that a proper sterilization temperature has not been reached.

Accordingly, what has been described is a simple and efficient contact lens holder which provides indication of whether or not a desired sterilization temperature has been reached within the container of the contact lens holder. While the present invention has been illustrated with regard to a single specific embodiment or type of lens holder, it will be understood that other types may be employed, or that numerous variations and modifications may be effected without departing from the spirit and scope of the novel concepts disclosed and claimed herein.

The invention is claimed as follows:

1. In the combination of a contact lens holder including a container body, a closure member for said container body and a central support member carried by said closure member and positionable within said container body, said central support member including means for receiving contact lenses to be sterilized by the subjecting thereof to a sterilizing temperature within said container body, said central support including a relatively rotatable transparent vessel, a quantity of eutectic material container within said vessel which material will be substantially solid at temperatures below said sterilization temperature and will become liquid at said sterilizing temperature or above, said quantity of eutectic material only partially filling said vessel, means rotatably mounting said vessel to said central support for rotative movement about a horizontally disposed axis, and means for releasably fixing the position of said vessel relative to said horizontal axis, such that prior to sterilization, said vessel being positioned with the solid eutectic material in an elevated orientation, such that upon achieving the sterilizing temperature, said eutectic material will become liquid and will flow to the bottom of said vessel, thereby providing a visual indication as to the achievement of said sterilizing temperature, with said rotatable mounting enabling said vessel to be repositioned for subsequent sterilizing operations.

2. The combination as defined in claim 1 wherein said means for receiving said contact lenses comprises oppositely facing concave surfaces for supporting contact lens elements, a pair of recessed cover elements pivotally mounted to said support member to overlie said concave surfaces and any lens elements thereon.

3. The combination as defined in claim 2 wherein said transparent vessel provides said oppositely facing concave surfaces.

4. The combination as defined in claim 1, wherein said means for releasably fixing the position of said vessel comprises, a handle joined with said vessel for effecting selective rotation thereof, and protuberances and detent means on said vessel and said support member, which when engaged will fix the position of said vessel, said engagement being releasable to reposition said vessel as desired.

* * * * *